(12) United States Patent
Baltas et al.

(10) Patent No.: US 7,425,194 B2
(45) Date of Patent: Sep. 16, 2008

(54) TEMPLATE-ASSEMBLY FOR EFFECTING RADIATION TREATMENT IN AN ANIMAL BODY

(75) Inventors: Dimos Baltas, Darmstadt (DE); Johann Kindlein, Toenisvorst (DE); Oscar Boel, Goirle (NL); Albert Dirk Adrianus Koster, Utrecht (NL); Emil Matthijs Buijs, Veenendaal (NL)

(73) Assignee: Nucletron B.V., Veenendaal (NL)

( * ) Notice: Subject to any disclaimer, the term of this patent is extended or adjusted under 35 U.S.C. 154(b) by 516 days.

(21) Appl. No.: 10/462,719

(22) Filed: Jun. 17, 2003

(65) Prior Publication Data

US 2004/0059177 A1    Mar. 25, 2004

(30) Foreign Application Priority Data

Jun. 17, 2002    (DE) .................................. 02077436
Jun. 5, 2003     (DE) .................................. 03076748

(51) Int. Cl.
*A61N 5/00*    (2006.01)

(52) U.S. Cl. ......................................................... 600/3

(58) Field of Classification Search ................. 600/1–8; 604/116; 606/130, 150; 250/497.1
See application file for complete search history.

(56) References Cited

U.S. PATENT DOCUMENTS 5,103,395 A * 4/1992 Spako et al. ................. 600/431
5,391,139 A 2/1995 Edmundson
5,868,757 A 2/1999 Koutrouvelis
5,931,786 A 8/1999 Whitmore, III et al.
6,036,632 A 3/2000 Whitmore, III et al.
6,095,975 A 8/2000 Silvern
6,200,255 B1 3/2001 Yu
6,387,034 B1 5/2002 Lee
6,500,109 B2 12/2002 Tokita et al.
6,659,956 B2 * 12/2003 Barzell et al. ................ 600/461
6,752,753 B1 * 6/2004 Hoskins et al. ................ 600/7
6,786,593 B2 * 9/2004 Zelman ...................... 351/103
2002/0038117 A1 3/2002 Tokita et al.
2002/0177807 A1 * 11/2002 Huitema et al. ............. 604/116

FOREIGN PATENT DOCUMENTS

WO     WO 01/28631 A1    4/2001

* cited by examiner

*Primary Examiner*—Charles A. Marmor, II
*Assistant Examiner*—Christine D Hopkins
(74) *Attorney, Agent, or Firm*—Birch, Stewart, Kolasch & Birch, LLP

(57) ABSTRACT

A template-assembly for effecting radiation treatment within an animal body by implanting one or more hollow needles at a desired location within the animal body includes a template frame being mountable to a stepping device of a radiation treatment device. The template frame has a needle guiding component having a plurality of guiding apertures for guiding the one or more hollow implant needles towards the desired location within the animal body. The template-assembly has a needle fixation component for fixating one or more of the implanted needles relative to the animal body, wherein the needle fixation component can be sutured to the skin of the animal body.

19 Claims, 7 Drawing Sheets

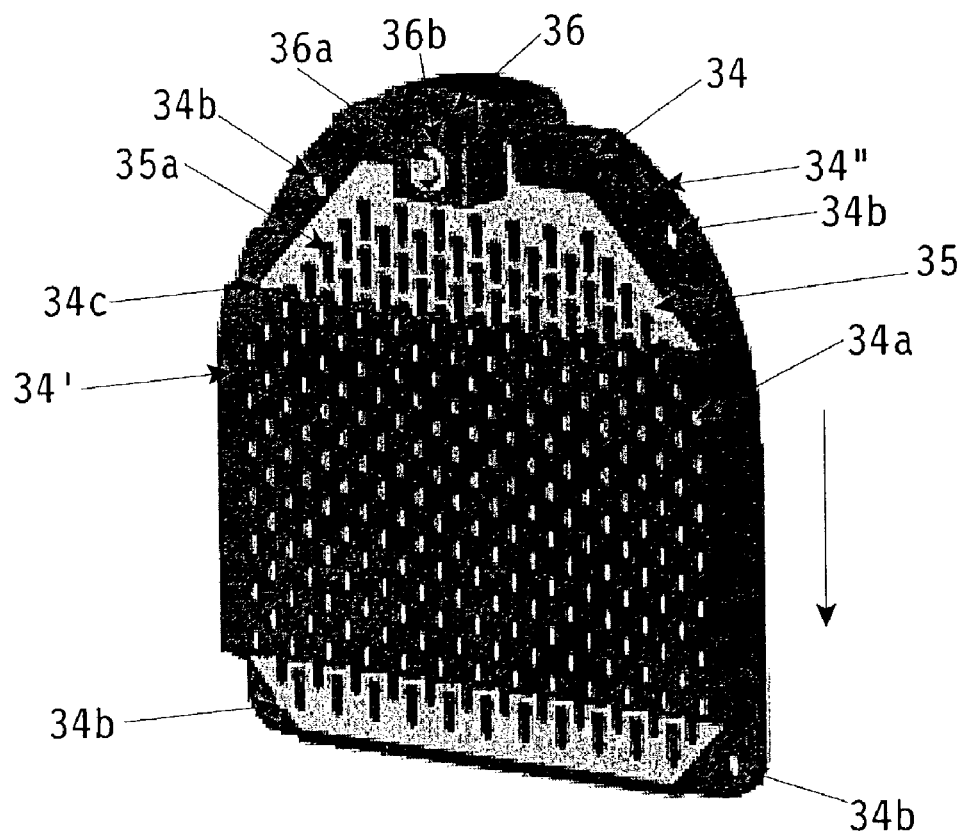
Fig. 4a
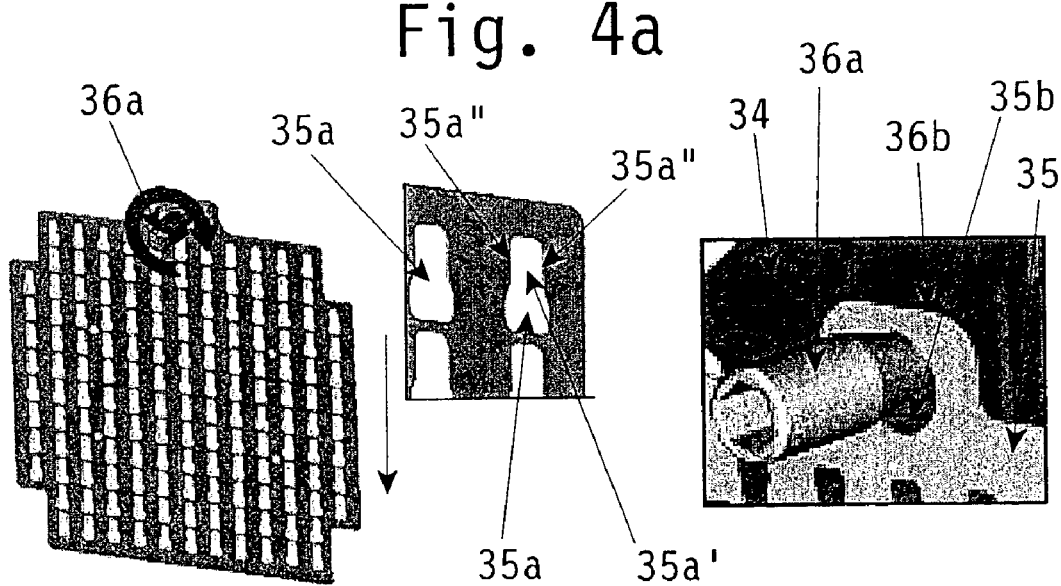
Fig. 4b
Fig. 4c

TEMPLATE-ASSEMBLY FOR EFFECTING RADIATION TREATMENT IN AN ANIMAL BODY

The invention relates to a template-assembly for effecting radiation treatment within an animal body by implanting one or more hollow needles at a desired location within said animal body comprising a template frame being mountable to a stepping device of a radiation treatment device, said template frame having a needle guiding component having a plurality of guiding apertures for guiding said one or more hollow implant needles towards said desired location within said animal body.

The invention relates also to a radiation treatment device provided with a template-assembly according to one or more of the preceding claims.

The nowadays objective of radiation therapy is to deliver a curative radiation dose to the target, for example a tumour, while preserving normal tissue of the animal body/patient from undesired and harmful radiation. This objective can now be achieved with a high degree of sophistication using highly accurate three-dimensional imaging techniques. With these techniques it is possible to obtain a proper definition of the anatomy of said animal body and more in particularly the area to which the radiation treatment has to be administrate.

However certain radiation treatment techniques and more in particularly brachytherapy treatments have not yet fully benefit from these important new developments in acquiring three-dimensional information of the animal body, where such radiation treatments are to be performed. More in particularly in brachytherapy radiation treatments high dose rate (HDR) energy emitting sources are used which are implanted in the animal body using catheters or hollow needles, which are inserted within an animal body towards the target location. From the implant positions of the implant needles it is assumed that if the dose distribution of the radiation being administered is covering the hollow implant needles, said dose distribution also covers said part of said animal body to be treated.

A template-assembly according to the above preamble is for example known from U.S. Pat. No. 6,500,109 B2.

A drawback of the template-assembly of U.S. Pat. No. 6,500,109 B2 is that the force exerted on the implant needle during insertion and/or removal is not controllable. The insertion force and removal force exerted on the hollow implant needle during insertion and removal is greatly dependent on the amount of friction (resistance), the needle meets from the tissue surrounding the needle and from the needle guiding method. Due to the uncontrollable character of the resistance force the implant needle meets during insertion and/or removal, the exact location within said animal body can not be guaranteed. Especially after insertion the position of the hollow implant needle within said animal body can not often be maintained, due to return friction forces exerted on said hollow implant needle due to unexpected movements of the patient.

The present invention aims to avoid the above-identified drawbacks and to provide a needle-assembly, wherein the exact position of the implant needles within the animal body is maintained under all circumstances, irrespective of the impact of the tissue surrounding said needle and/or movements of the patient which would lead to a reorganisation of the hollow needles within the patient's body.

The template-assembly according to the invention thereto comprises a needle fixation component for fixating one or more of said implanted needles relative to said animal body, wherein said needle fixation component can be sutured to the skin of said animal body. More in particularly said needle fixation component fixates said needles against displacement in the direction of implant.

With these features according to the invention the exact position of the hollow needles as preplanned within the patient's body is maintained at all time. Moreover said positions are not disturbed or altered due to unexpected movements of the patient's body and/or due to the influence of the tissue surrounding said hollow needles.

The undisturbed orientation of the implanted hollow needles is further improved by the possibility of suturing the needle fixation component to the skin of the patient. A further reduction of weight and an improvement of the comfort of the patient during treatment is obtained as according to the invention said needle fixation component is detachable mountable to said template-assembly. Therefor it is no longer necessary to suture the needle guiding component (part of the needle frame) to the patient.

To this end the cooperation between the needle fixation component and the template-assembly is characterized in that said needle fixation component is provided with two or more openings, which openings interact with two or more pins extending from said template-assembly. Especially said needle fixation component can be sutured to said animal body using said two or more openings.

More in particularly said needle fixation component comprises a disposable protective layer for protecting the skin of said animal body. The feature of such skin protective layer avoids the perineal skin to become too irritated. Thereto said skin protective layer consists of a thin oxygen-permeable dressing. This ensures the needle and suturing wounds to heal quicker, especially when the skin is healthy. These features are important for the patient's recovery and add significantly to the patient's comfort.

Likewise said skin protective layer is provided with a plurality of apertures extending there through, said plurality of apertures being conformal to said plurality of guiding apertures of said needle guiding component. However the skin protective layer can also exhibit no apertures, but manufactured from a material that is easily to be penetrated by a needle.

As the exact position of the hollow implanted needles are maintained irrespective of "disturbances" also a correct positioning of one or more energy emitting sources, for example radioactive seeds inserted through said hollow implanted needle towards a desired location within said portion of the animal body, is obtained, which positions conform or actually match the positions as preplanned by suitable radiation treatment doses planning software.

Thus with these features of the invention a radiation dose distribution is obtained more accurately matching the preplanned dose distribution.

More in particularly said needle fixation component is provided with a plurality of apertures extending there through, said plurality of apertures being conformal to said plurality of guiding apertures of said needle guiding component.

In a preferred embodiment of the template-assembly according to the invention, said needle fixation component consists of two or more segments, each provided with a conformal set of plurality of apertures extending there through, and wherein for fixating purposes at least one of said segments is movable with respect to the other segment(s).

More in particularly said segments are positioned in line and at some distance from each other or said segments are positioned in line and in an abutting manner against each other. In this latter embodiment according to the invention an effective fixation of the inserted hollow implant needles can be obtained as the apertures of one of said segments are keyhole-shaped.

For an easy and proper displacement of at least one of the segments with respect to the other segment(s) the segments each comprise a fixation opening being in line with each other through which aligned fixation openings an elongated element is mountable and being capable of rotating about its elongated axis and wherein its circumferential surface is partly eccentrically shaped. By rotating the fixation element the eccentrically shaped part of the circumferential surface abuts the inner edge of the fixation opening of one of said segments and displaces said segment with respect to the other segment(s).

As in one embodiment the fixation opening of the segment to be displaced with respect to the other segment(s) is oval shaped in horizontal direction an accurate and easy displacement of said segment in vertical direction with respect to the other segment(s) is obtained.

In a further embodiment of the template-assembly according to the invention said segments are positioned in one geometrical plane and in an adjacent manner against each other. With these features said segments comprise adjacent engaging edges, which engages edges may exhibit a sawtooth profile or a curved profile.

A very specific embodiment exhibiting these features is characterized in that said needle fixation component consists of four coplanar engaging segments.

In another embodiment according to the invention each aperture of said needle fixation component is surrounded by a protruding cone-shaped hollow needle clamping element. After insertion of a hollow implant needle through such aperture, said clamping element engages said hollow needle in a clamping matter fixating said hollow needle relative to the animal body.

To facilitate the clamping effect of said clamping element on a hollow needle inserted through said aperture, each cone-shaped hollow needle clamping element is provided with two protruding parts extending parallel to each other, which protruding parts are separated by two slits.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

With reference to the accompanying drawings which are given by way of illustration only, and thus are not limitative of the present invention, and wherein the invention will now be explained in more detail:

FIGS. 4a-4c and 5a-5b detailed aspects of FIG. 3;

DETAILED DESCRIPTION OF THE INVENTION

Figure 1:
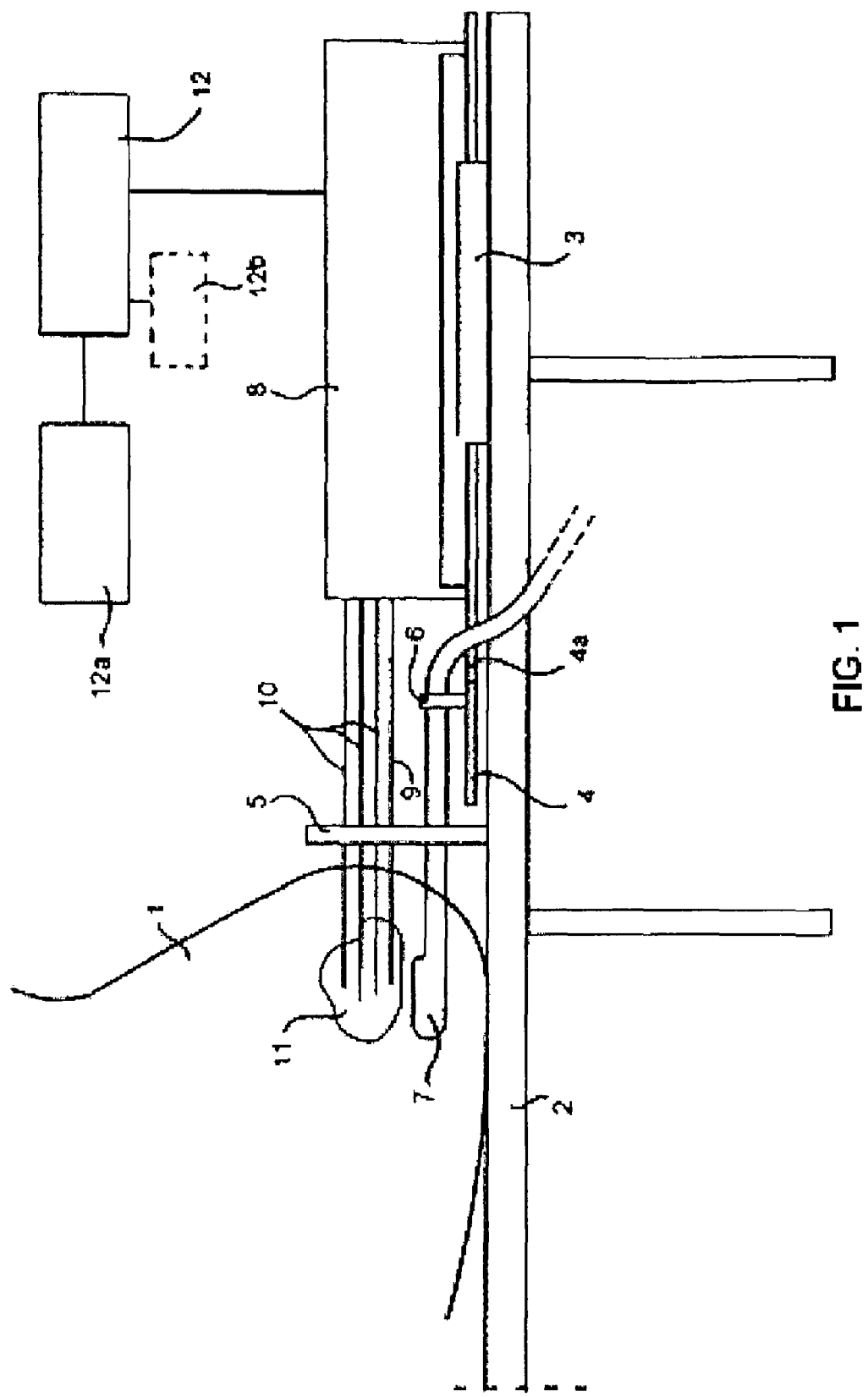
FIG. 1 shows in very schematic form a known radiation treatment device using a known template-assembly.

FIG. 1 shows in very schematic form various elements of a known radiation treatment device using a template-assembly for implanting one or more energy emitting sources, e.g. radioactive seeds towards a desired location within an animal body, for example into a prostate gland.

A patient 1 is shown lying in lithotomy position on a table 2. Fixedly connected to the table 2 is a housing 3. Housing 3 comprises a stepping device 4 to move rod 4a stepwise. A template-assembly 5 is connected or mounted to the table 2, which template-assembly is provided (not shown) with a plurality of guiding holes through which holes hollow needles 9, 10 can be positioned relative to the patient. By means of a holder 6 a transrectal imaging probe 7 is fixedly connected to said rod 4a, which is moveable in a direction towards and from the patient by means of the stepping device 4. The imaging probe 7 can be an ultrasound probe.

A needle 9 is used for fixing the prostate gland 11 in position relative to the template-assembly 5. A number of needles 10 is fixed into position through the template-assembly 5 in the prostate gland 11. The template-assembly 5 determines the relative positions of the needles 10 in two dimensions.

The known device shown in FIG. 1 operates as follows. A patient 1 is under spinal or general anaesthesia and lies on the operating table 2 in lithotomy position. The (ultrasound) imaging probe 7 is introduced into the rectum and the probe is connected via signal line 7a with a well known image screen, where an image may be seen of the inside of the patient in particular of the prostate gland 11 as seen from the point of view of the imaging probe 7. The template-assembly 5 is attached to the stepping device 4, thereby insuring the correlation of the ultrasound image geometry and the template-assembly 5. Subsequently further needles 10 are introduced in the body and the prostate gland under ultrasound guidance one by one.

Moving the imaging probe with the drive means 4 longitudinally within the rectum controls the needle depths of each needle 10. After all needles 10 have been placed, their positions relative to the prostate gland 11 are determined in at least one of several known ways. In a known way the therapy planning module 12a determines how the needles 10 are to be placed in the prostate and how many radiation emitting sources are to be placed in what order in each of the needles 10. The information about the desired placement of the radioactive seeds in the needles 10 is used to control the seed loading unit 8.

Figure 2:
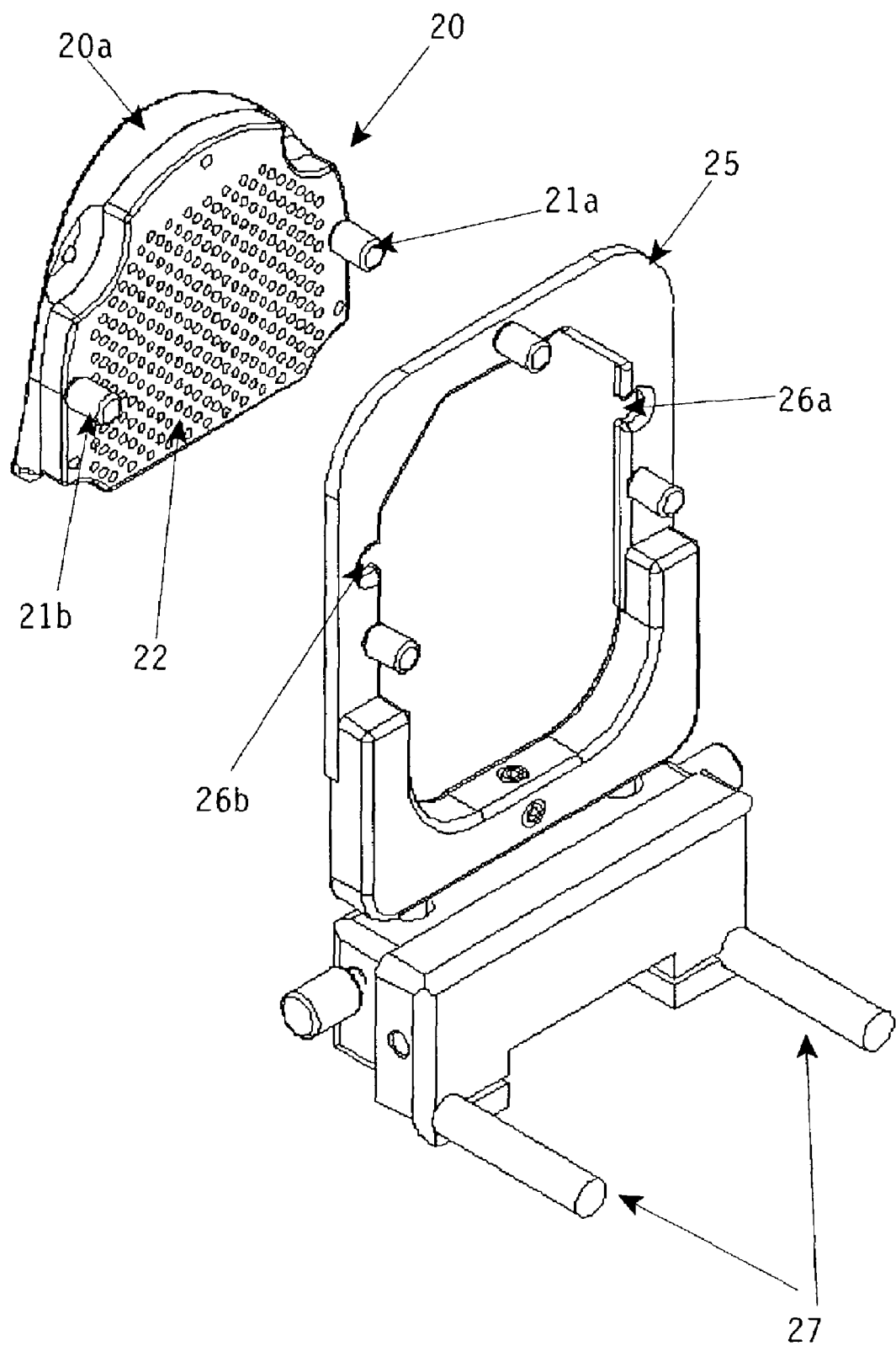
FIG. 2 a first embodiment of a template-assembly according to the invention.

In FIG. 2 a template-assembly is disclosed for use in a real time radiation treatment planning system according to the invention. Especially the needle guiding component 20 is detachable from a template frame 25, which frame is connected with the stepper means for displacing the imaging means as described in connection with FIG. 1.

According to the invention said needle guiding component 20 has a grid configuration with needle holes 22 at an intermediate distance of 3.5 mm seen in diagonal direction. In another embodiment the needle guiding component has a grid configuration with needle holes at an intermediate distance of 2.5 mm seen in orthogonal direction.

A more specific embodiment of the needle guiding component is disclosed in FIG. 2, where said needle guiding component 20 is detachable from the frame 25. Frame 25 is connected with the stepper means as described above. For a good connection and orientation of the frame 25 and needle guiding component 20 in relation to the device of FIG. 1 the frame 25 is provided with alignment pins 27 which cooperate with corresponding openings (not shown) in the device of FIG. 1.

The needle guiding component 20 has a saddle shaped body 20a, which fits with the frame 25 as shown in FIG. 2. For alignment purposes the needle guiding component 20 is provided with notches 21a-21b, which cooperate with corresponding holes 26a-26b present in the circumference of frame 25.

Figure 3:
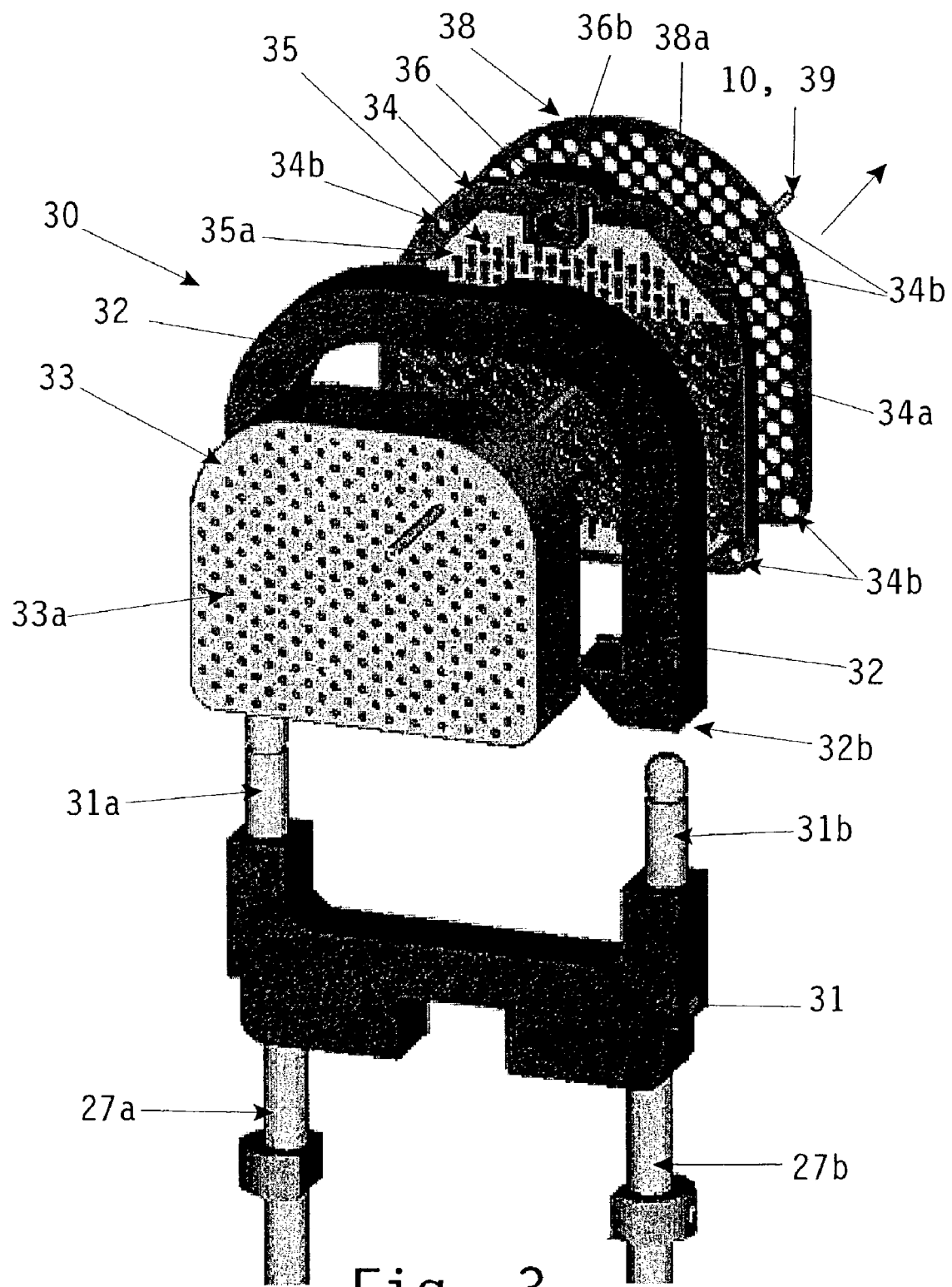
FIG. 3 a further embodiment of a template-assembly according to the invention.

In FIG. 3 an embodiment of the template-assembly according to the invention is disclosed. A mounting frame 31 which is mountable to or part of a stepping device of a radiation treatment device (not shown) uses alignment pins 27 for supporting the template-assembly. More in particular it is mountable to the stepper means of a known radiation treatment device such as disclosed in FIG. 1. Reference is also made to FIG. 2 wherein likewise parts are depicted by the same reference numerals.

The mounting frame 31 is provided with alignment pins 31a-31b which interact in corresponding mounting openings 32a-32b present in a template frame 32. Said template-frame 32 serves to contain or hold a needle guiding component 33 provided with a plurality of guiding apertures 33a. Said apertures 33a serve to guide one or more hollow implant needles 10, 39 towards a desired location within an animal body. As already described in conjunction with FIGS. 1 and 2 through said implanted hollow implant needle 10, 39 one or more energy emitting sources, for example radioactive seeds, are inserted towards said desired location within the animal body in order to administer a certain amount of radiation with a specific radiation dose distribution.

Preferably the needle guiding component 33 is manufactured from a plastic or a metal like aluminium, which materials are light, easy to clean and more in particular sterilisation-prove. On the other end, this needle guiding component can be disposable and intended for single use only.

According to the invention the template-assembly 30 as depicted in FIG. 3 is provided with a needle fixation component 34-35, which serves to fixate the inserted and implanted hollow needle 10, 39 against undesired displacements relative to the animal body, wherein the radiation treatment has to be performed.

In the embodiment as disclosed in FIG. 3 the needle fixation component fixates the implant needles 10, 39 against displacements in the direction of implant and is provided with plurality of apertures extending there through.

In this embodiment the needle fixation component consists of two segments, depicted with reference numerals 34 and 35. The segments 34-35 are each provided with a conformal sets of plurality of apertures extending there through, which apertures are depicted with reference numbers 34a and 35a respectively. For a proper operation of the needle fixation component, said plurality of apertures conform the plurality of guiding apertures 33a of said needle guiding component 33.

As clearly shown in FIG. 3 and the detailed views of FIGS. 4a-4c said segments 34-35 are positioned in line of the direction of implant and are positioned against each other in an abutting manner. As the detailed views of FIGS. 4a-4c disclose, the apertures 35a of segment 35 are keyhole-shaped. This is clearly shown in FIG. 4b, wherein the aperture 35a exhibits an elongated shape with a part 35a having a larger diameter and a part 35a' having a smaller diameter or dimensions.

The fixating principle of the embodiment as disclosed in FIG. 3 and FIGS. 4a-4c is as follows. Segment 35 of the needle fixation component 34-35 has to be displaced relative to the segment 34 in vertical direction as depicted by the arrow in FIG. 4. As clearly shown in FIG. 4a the segment 34 having a front face 34' and a rear face 34" is provided with a slit or slot 34c in which the other segment 35 is slidable accommodated. The displacement of segment 35 with the keyhole-shaped apertures 35a within said slit 34c relative to the other segment 34 of the needle fixation component 34-35 is performed by means of a conically shaped screw 36a. This screw 36a fits in a threaded opening 36b present in a notch 36 at the top of the segment 34 as well as in an opening 35b of the needle fixation component 34-35.

By turning or fastening the screw 36a into the threaded opening 36b segment 35 is displaced in vertical direction with respect to segment 34 due to the conical shape of the screw 36a. The implant needles 10, 39 inserted through the guiding apertures 33a and through the apertures 35a and 34a are to be locked by means of pressure exerted by the edges 35a" of the keyhole-shaped aperture 35a' on the circumferential surface of the needle 10, 39.

Figure 5A:
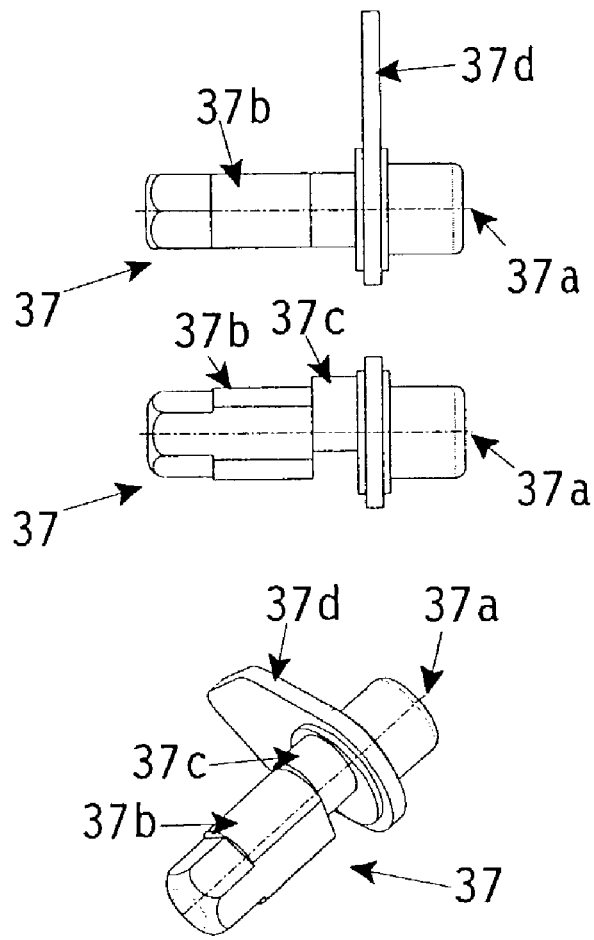
Figure 5B:
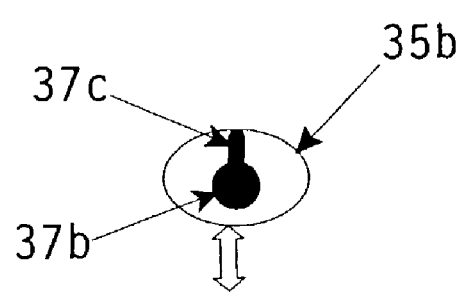

In FIGS. 5a-5b another embodiment is disclosed wherein an easy and proper displacement of at least one 35 of the segments with respect to the other segment(s) 34 is obtained. In this embodiment the segments 34-35 each comprise a fixation opening 36b-35b being in line with each other through which aligned fixation openings 36b-35b an elongated element 37 is mountable. Said element 37 is capable of rotating about its elongated axis 37a and is provided with a circumferential surface 37b, that is partly eccentrically shaped (see reference numeral 37c).

Said eccentrically shaped part 37c of said circumferential surface 37b is only in contact with the inner edge of opening 35b of said segment 35. By rotating the fixation element 37 around its axis 37a, the eccentrically shaped part 37c of the circumferential surface 37b abuts against the inner edge of the fixation opening 35b and displaces said segment 35 with respect to the other segment 34.

The vertical displacement of segment 35 is possible as opening 35b has an oval shape in horizontal direction as shown in FIG. 5b. With the vertical displacement of segment 35 with respect to segment 34 the implanted needles 10, 39 are to locked by means of pressure exerted by the edges 35a" of the keyhole-shaped aperture 35a' on the circumferential surface of the needle 10, 39.

The extension part 37d of said element 37 serves as an indicator for the user to indicate whether the needle fixation component 34-35 is set in its locking or in unlocking position.

With these both constructions as shown in FIGS. 3, 4a-4c and 5a-5b any undesired displacement of the implant needle 10, 39 is avoided especially in the directions of implant. Especially with this embodiment it is possible to fixate one needle but even a large group of needles 10, 39 inserted through the needle guiding component 33 in one operation. The fixation avoids therefore an undesired displacement of the needles 10, 39 and the energy emitting sources inserted in it during administering radiation therapy to the desired location within the animal body. Thus the radiation dose and the distribution thereof accurately conforms the radiation distribution dose as preplanned prior to performing the radiation treatment.

According to a further aspect of the template-assembly according to the invention said needle fixation component 34-35 is detachable mountable to the template-assembly 30. To this end, the needle fixation component 34-35 is provided with four openings 34b in segment 34, which openings 34b cooperate with corresponding pins (not visible), which extend or protrude from the template-frame 32.

This results in a compact template-assembly with an additional needle fixation component 34-35 with limited constructional space. Furthermore, the whole assembly can be manufactured from light materials like plastics or a metal. More in particular, the segment 35 with the keyhole-shaped openings 35a is manufactured from steel due to its firmness and rigidity. The apertures 35a are manufactured in the steel plate 35 using a photo-etching technique.

In another aspect of the invention the needle fixation component 34, 35 is as stated before detachable from the template-assembly 30 in order to suture the needle fixation component 34-35 using the openings 34b to the skin of the patient. This construction ensures a proper orientation with respect to the body of the patient.

In order to avoid a discomforting irritation of the perineal skin of the animal body the detachable needle fixation component 34-35 can be equipped with a protective layer 38 which is preferably manufactured from a thin oxygen-permeable dressing. The application of the protective layer 38 between the needle fixation component 34-35 and the perineal skin of the patient allows a much quicker healing of the needle insertion and suturing wounds thus improving the comfort for the patient significantly. Likewise the protective layer 38 is provided with a plurality of skin apertures 38a, which conform the plurality of guiding apertures 33 present in the needle guiding component 33.

However the skin protective layer 38 can also exhibit no apertures, but manufactured from a material that is easily to be penetrated by a needle.

The protective layer 38 is likewise provided with openings 34b, which are in alignment with the openings 34b of the needle fixation component 34 allowing a quick and aligned mounting to the needle fixation component 34-35 and the template-assembly 30. Moreover in the event the needle fixation component 34-35 is detached from the template-assembly 30 the aligned openings 34b of both the skin protective layer 38 and the fixation segment 34 are used for suturing the needle fixation component 34-35 with the skin protective layer 38 to the perineal skin of the patient.

In another embodiment both the template-assembly 30 and the needle fixation component 34-35 can be provided with magnetic coupling elements.

Figure 6:
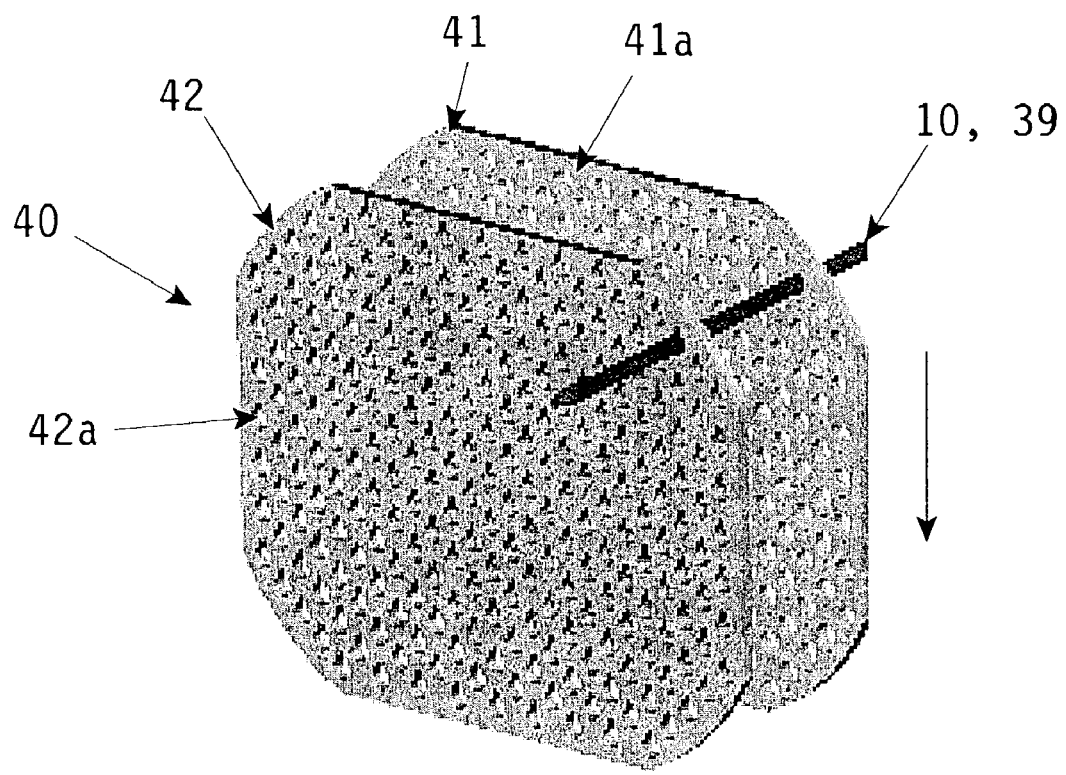
FIGS. 6-8 further embodiments of a template-assembly according to the invention.

In FIG. 6 another embodiment of the needle fixation component according to the invention is disclosed. Here the needle fixation component 40 consists of two segments 41-42, which are positioned in line and at some distance from each other. Each segment 4142 is provided with a plurality of apertures 41a-42a, the layout of these apertures being conformal to the layout of the apertures 33a of the needle guiding component 33.

According to the invention the needle fixation component 40 operates as follows. By displacing one of the two segments 41 or 42 with respect to the other segment, the apertures 33a, 41a and 42a are no longer in direct alignment making the insertion of a needle through two corresponding apertures 41a-42a difficult and locking the needles 10, 39 already inserted.

Also with this embodiment it is possible to fixate one needle, but even a large group of needles 10, 39 inserted through the needle guiding component 33 in one operation.

Figure 7:
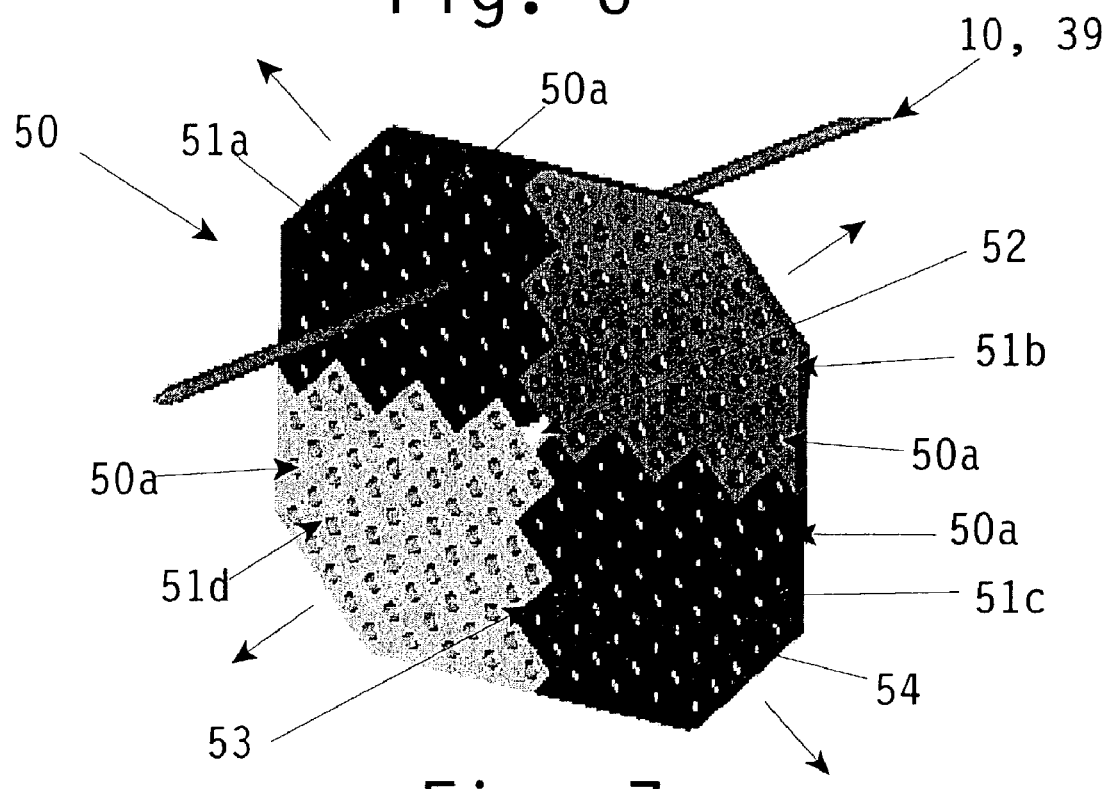

In FIG. 7 another embodiment of the needle fixation component according to the invention is disclosed. Here wherein the needle fixation component 50 consists of four segments 51a-51d, which segments are positioned in one geometrical coplanar plane and in an adjacent manner against each other. All four segments 51a-51d are provided with a plurality of apertures 50a being conformal to said plurality of guiding apertures 33a in said needle guiding component 33. The operation of die needle fixation component according to FIG. 7 operates as follows.

All four segments 51a-51d are positioned in an adjacent manner with respect to each other, such that the adjacent edge 53 of segment 51b and edge 54 of segment 51c are in an engaging manner. As the FIG. 7 clearly shows, said engaging edges 53, 54 exhibit a sawtooth profile. However, also other profiles such as a curved profile are suitable for the invention.

The segmented needle fixation component 50 comprises a center center opening 52 through which a cone-shaped pin (e.g. a cone-shaped screw, not shown) can be placed. By forcing said cone-shaped pin through the center opening 52, for example by turning the cone-shaped screw, the four segments 51a-51d are displaced in a direction away from each other as depicted by four arrows in FIG. 7. The displacement of the four segments 51a-51d in the direction of the arrows depicted result in a fixation of the needles 10, 39 with respect to the needle guiding component 33 and the animal body in which the needles 10, 39 are implanted.

Again also with this embodiment one needle or even a large group of needles 10, 39 inserted through the needle guiding component 33 can be fixated in one operation.

Figure 8:
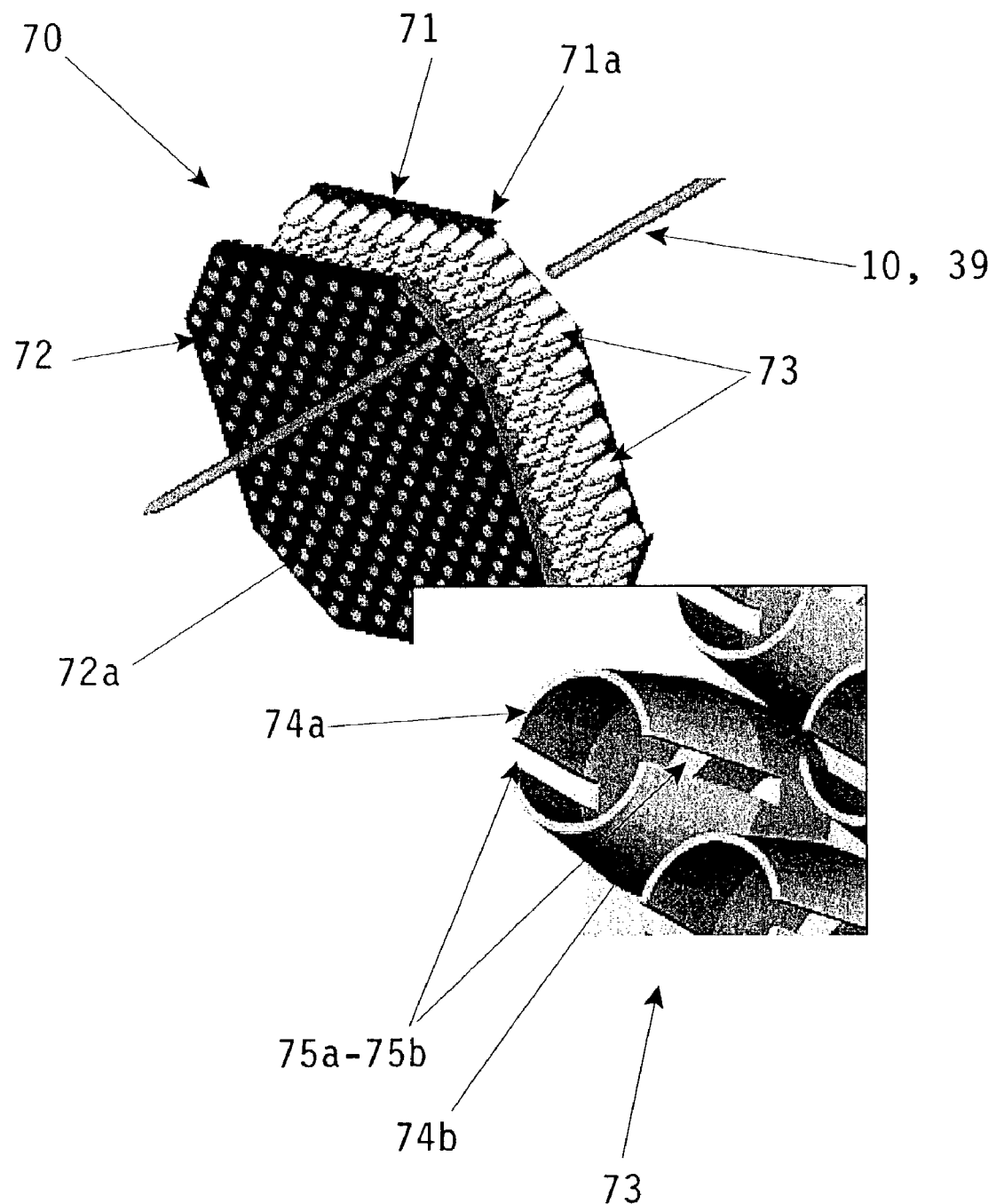

Yet another embodiment of the needle fixation component according to the invention is disclosed in FIG. 8. Here the needle fixation component consists of two segments 71-72, which are positioned in line and at some distance from each other. Both segments 71-72 are provided with a plurality of apertures 71a-72a, which apertures are conformal to each other and to the apertures 33a of said needle guiding component 33.

For obtaining a proper fixation of the needle 10, 39 each aperture 71a of said needle fixation component 71 is surrounded by a protruding cone-shaped hollow needle clamping element 73. Said needle clamping element 73 is provided with two protruding parts 74a-74b, which extend parallel to each other and are separated by two slits 75a-75b. The two protruding parts 74a-74b are more or less resilient and allow a proper insertion of the needle 10, 39 through the aperture 71a. However, the protruding parts 74a-74b exhibit a tight fit in two opposite directions perpendicular to the circumferential surface of the hollow implant needled 10, 39 and hold and maintain the needles in a fixating manner.

Also with this embodiment it is possible to fixate one needle or a large group of needles 10, 39 inserted through the needle guiding component 33 in one operation.

For a proper interpretation of the invention it will be apparent for the skilled man in the art, that also the embodiments of the needle fixation component as shown in FIGS. 6-8 can combined with the skin protective layer 38 as described in relation with FIGS. 3, 4a-4c.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. Template-assembly for effecting radiation treatment within an animal body by implanting one or more hollow needles at a desired location within said animal body, said template-assembly comprising:

a template frame being mountable to a stepping device of a radiation treatment device, said template frame having a needle guiding component having a plurality of guiding apertures for guiding said one or more hollow implant needles towards said desired location within said animal body, a needle fixation component for fixating one or more of said implanted needles relative to said animal body, said needle fixation component being provided with a plurality of apertures extending therethrough, said plurality of apertures being conformal to said plurality of guiding apertures of said needle guiding component and being operable in a first, unlocking position for allowing at least one needle to be implanted and a second, locking position for fixating at least one needle relative to said animal body, wherein said needle fixation component is detachably mountable to said template-assembly and comprises at least a first segment and a second segment, said second segment being displaceable in said first, unlocking position and second, locking position with respect to said first segment and wherein said needle fixation component is provided with suturing means for suturing said needle fixation component to the skin of said animal body when being detached from said template-assembly.

2. The template-assembly according to claim 1, wherein both first and second segments comprise a fixation opening being in line with each other through which aligned fixation openings an elongated element is mountable, said elongated element being capable of rotating about an elongated axis of the elongated element and wherein a circumferential surface of the elongated element is partly eccentrically shaped.

3. The template-assembly according to claim 2, wherein the fixation opening of the second segment is oval shaped in a horizontal direction.

4. The template-assembly according to claim 1, wherein said second segment is a plate having at least one plate-segment.

5. The template-assembly according to claim 4, wherein said second segment has at least two plate-segments.

6. The template-assembly according to claim 5, wherein said plate-segments are positioned in line and at some distance from each other.

7. The template-assembly according to claim 5, wherein said plate-segments are positioned in line and in an abutting manner against each other.

8. The template-assembly according to claim 5, wherein said plate-segments are positioned in one geometrical plane and in an adjacent manner against each other.

9. The template-assembly according to claim 8, wherein said plate-segments comprise adjacent engaging edges.

10. The template-assembly according to claim 9, wherein said engaging edges exhibit a sawtooth profile.

11. The template-assembly according to claim 9, wherein said engaging edges exhibit a curved profile.

12. The template-assembly according to claim 8, wherein said needle fixation component consists of four coplanar engaging segments.

13. The template-assembly according to claim 1, wherein said needle fixation component fixates said one or more needles against displacements in the direction of implant.

14. The template-assembly according to claim 1, wherein said needle fixation component is provided with two or more openings, which openings interact with two or more pins extending from said template-assembly.

15. The template-assembly according to claim 1, wherein said needle fixation component and said template-assembly are provided with magnetic coupling elements.

16. The template-assembly according to claim 14, wherein said needle fixation component can be sutured to skin of said animal body using said two or more openings.

17. The template-assembly according to claim 1, wherein said needle fixation component comprises a disposable protective layer for protecting the skin of said animal body.

18. The template-assembly according to claim 17, wherein said skin protective layer is provided with a plurality of apertures extending therethrough, said plurality of apertures being conformal to said plurality of guiding apertures of said needle guiding component.

19. Radiation treatment device provided with the template-assembly according to claim 1.

* * * * *